United States Patent

Moedritzer

[11] 4,072,653
[45] Feb. 7, 1978

[54] POLYMERIC PHOSPHINE OXIDE FLAME RETARDANTS

[75] Inventor: Kurt Moedritzer, Webster Groves, Mo.

[73] Assignee: Monsanto Company, St. Louis, Mo.

[21] Appl. No.: 688,205

[22] Filed: May 20, 1976

[51] Int. Cl.$^2$ .................... C08K 5/53; C07F 9/02
[52] U.S. Cl. ................... 260/45.7 P; 260/2 P; 260/606.5 P; 260/857 R; 260/860
[58] Field of Search ............ 260/606.5 P, 45.7 P, 260/2 P, 860, 857 R

[56] References Cited

U.S. PATENT DOCUMENTS

| | | | |
|---|---|---|---|
| 3,044,984 | 7/1962 | Bloomfield | 260/2 P X |
| 3,158,642 | 11/1964 | Chapin et al. | 260/2 P X |
| 3,830,771 | 8/1974 | Cohen et al. | 260/860 X |
| 3,927,231 | 12/1975 | Desitter et al. | 260/860 X |
| 3,931,099 | 1/1976 | King | 260/860 X |
| 3,993,623 | 11/1976 | Moedritzer et al. | 260/857 R X |

Primary Examiner—Lewis T. Jacobs
Attorney, Agent, or Firm—Herman O. Bauermeister

[57] ABSTRACT

Polymeric phosphine oxides having the formula

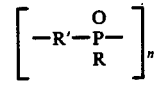

where R is an alkyl group of from 1 to 20 carbon atoms, or an aryl group of from 6 to 20 carbon atoms, R' is a phenylene or naphthylene group, and n is from 2 to 50 or preferably 5 to 25. The invention also relates to compositions of such polymeric phosphine oxides with organic polymers such as polyesters, e.g. ethylene terephthalate and polyamides, e.g. hexamethylene adipamide. The combination of the present polymeric phosphine oxides with the organic polymers makes it possible to obtain flame retardant products useful in many applications such as for carpeting and clothing.

9 Claims, No Drawings

POLYMERIC PHOSPHINE OXIDE FLAME RETARDANTS

FIELD OF THE INVENTION

The present invention relates to novel polymeric phosphine oxides and combinations of such polymeric phosphine oxides with organic polymers such as polyesters, e.g. polyethylene terephthalate, and polyamides, e.g., hexamethylene adipamide. The physical or chemical combination of the present polymeric phosphine oxides with the organic polymers makes it possible to obtain flame retardant products, for example fibers suitable for carpeting and clothing. Specifically the invention relates to novel phosphine polymers having the formula

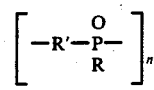

and R is an alkyl group of 1 to 20 carbon atoms, or an aryl group of 6 to 20 carbon atoms, R' is a phenylene or naphthylene group and $n$ is from 2 to 50 units, or preferably 5 to 25.

BACKGROUND OF THE INVENTION

Many flame retarding agents and methods of application have been developed in attempts to obtain flame resistant textile materials and thermoplastic or thermosetting resin compositions.

The production of organic resin compositions which are flame retardant is of considerable commercial importance. For example, such articles as fibers, films and the like are required, or are at least desired, to be resistant to fire and flame and to possess the ability to endure heat without deterioration. The use of various materials incorporated into thermoplastic resins so as to improve the flame retardancy thereof has been known. Many compounds have been commercially available for such use, among them being chlorostyrene copolymers, chlorinated paraffin wax in admixture with triphenyl phosphate, chlorinated paraffins and antimony compounds, as well as antimony oxide-chlorinated hydrocarbon mixtures. A problem associated with these compounds has been, however, the fact that generally a large amount, i.e., upwards of 35 percent of additive, must be incorporated into the resin in order to make is sufficiently flame retardant. Such large amounts of additive may deleteriously affect the physical characteristics of the thermoplastic resin, as well as substantially complicating and increasing the cost of preparation thereof. A further problem is that these prior art additives tend to crystallize or oil out of the resin after a relatively short time of incorporation. The present invention relates to a group of compounds which may be added to thermoplastic resins in relatively small amounts and still produce satisfactory flame retardant compositions which will not crystallize nor oil out the resin after incorporation therein.

Phosphorus compounds have been employed in various flame retardant products. However when some of the compounds of the prior art are employed with dissolved or molten organic polymers such as polyesters and polyamides, for example in fiber production, difficulties are encountered.

Some types of organic polyphosphonate compounds when used in extrusion processes, such as in the fiber spinning of polyesters, e.g., polyethylene terephthalate or polyamides, e.g., nylon 6,6 have been found to cause cross-linking. This results in severe problems of nodule formation during the spinning operation, with the result that spinnerettes are clogged and fibers cannot be handled in drawing, heat treating, washing and dyeing operations. This is because the nodules cause irregularities and thick sections in the fibers, so that the spinning operations become impossible.

In contrast to such prior art, the present invention utilizes polymeric phosphine oxides having a repeating P(O)-R' linkage in the backbone of the polymer where R' is phenylene or naphthylene. These polymers have been found to be a useful combination with organic polymers e.g. ester or amide products, so that the modified organic polyester or polyamide can be melted and spun from an orifice to yield smooth fibers which are readily stretched and washed for utilization in weaving operations. The present modified organic polymers are also characterized by improved flame retardancy properties. The present polymeric phosphine oxides existing as polymeric resins are characterized by the general molecular structure as polymeric products

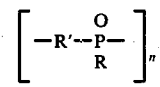

wherein R is an alkyl group of 1 to 20 carbon atoms or an aryl group of 6 to 20 carbon atoms, R' is phenylene or naphthylene, and $n$ is from 2 to 50, or preferably 5 to 25 units. The successive repeating units are provided by a P(O)R' linkage which is desirable for fire-retardant properties, and thermal stability. The R and the aromatic R'(e.g. naphthylene or phenylene) backbone groups may also have chlorine or bromine substituents. The R' group linked to the phosphorus and the continuation of the polymeric chain, may have such linkages in $o, m,$ or $p$ positions for the phenylene; and also in any positions e.g. 1, 4 or 2, 6, etc. of the naphthylene group.

The combination of atoms in the backbone of the polymeric molecular structure as-P(O)R'-, also imparts resistance to hydrolysis, since P-C bonds are less susceptible to hydrolyzing agents such as acids, bases, water and atmospheric humidity.

The general process for preparing the present polyphosphine oxides employs an Arbuzov rearrangement, catalyzed by a salt, e.g., nickel salt, at a temperature of 50° C to 300° C involving a monomeric compound having the general formula

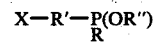

where X is chlorine or bromine, and R is an alkyl group of 1 to 20 carbon atoms or an aromatic group of 6 to 20 carbon atoms, and R" is an alkyl group of 1 to 20 carbon atoms. Examples of the monomer are

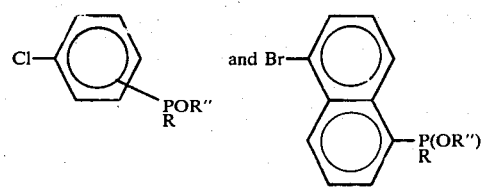

The polymerization occurs according to the general equation (with or without an inert solvent e.g. mesitylene)

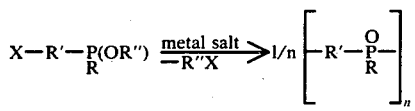

Specific examples are:

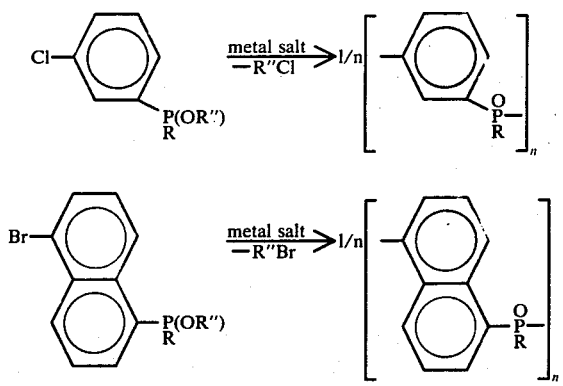

where X, R, R' and R" are as described above, and $n$ is a number from 2 to 50. The metal salt for this Arbuzov rearrangement is a Group VIII salt such as nickel chloride, cobalt bromide, an iron iodide, etc. The starting material is a haloaromatic phosphinite compound, having a phenyl or naphthyl substituted by X, which is a chlorine, or bromine radical and also optionally having alkyl substituents of 1 to 20 carbon atoms.

The invention also includes the combination of an organic polymer such as a polyester or a polyamide together with the above phosphine oxide polymer. The latter polymer may be used as an additive applied to the organic polymer in a molten state before spinning. However, the polyphosphine oxide may also be applied from a solution (e.g., in an aliphatic alcohol such as methanol, ethanol or iso-propanol, or a ketone such as methylethyl ketone) directly to sheets or other shaped forms, including fibers or fabrics of the organic polymer.

The invention also includes copolymers such as block copolymers of the above organic polymers together with the present phosphine oxide polymers made, e.g. as by ester interchange. The end groups e.g. R" of the polymeric chain can be an alkyl group and a halogen. However the terminal phosphorus may have on OR" group, permitting this latter group to be triply connected. This permits ester interchange and interpolymer formation with the organic polymer such as polyethylene terephthalate. Block copolymers can also be formed as a result of ester interchange using standard techniques.

The compounds of the present invention are useful in fire-retardant materials. The method of testing fireretardant properties is A.S.T.M. Designation D 2863-70, entitled "Standard Method of Test for Flammability of Plastics Using the Oxygen Index Method."

In the Oxygen Index (OI) testing procedure the relative flammability of a plastic material such as nylon, or polyethylene terephthalate is determined by measuring the minimum concentration of oxygen in a slowly rising mixture of oxygen and nitrogen that will just support combustion. Consequently the oxygen index expresses such minimum concentration of oxygen, expressed as volume percent, in a mixture of oxygen and nitrogen that will just support combustion.

The test is conducted by burning the material in a test column which is a heat resistant glass tube of 75mm minimum inside diameter and 450 mm minimum height. At the bottom of the tube is a bed of glass beads about 100mm deep to mix and distribute the gas mixture. Within the glass tube used as the test column there is a specimen holder to support the treated plastic material, while the apparatus is supplied with oxygen and nitrogen flow and control devices. The apparatus is also provided with an igniter which is a separate tube through which a combustible gas such as natural gas is used to ignite the test specimen. In the present testing program glass scrim supported molded sheets of nylon or polyethylene terephthalate ca. 0.2mm thick and about 25mm by 100mm in size are used as the test specimens which are prepared from nylon or polyethylene terephthalate powder and 1% to 20% by weight of the fire retardant additive; the data in the present work correspond to about 10% relative to the total mixture. Upon the molding of the organic polymer, e.g., nylon or polyethylene terephthalate, and the additive, an intimate admixture or melt of the molecules of the components is obtained.

In conducting the test, the specimen is clamped in the holder in the test column after which the desired initial concentration of oxygen is introduced to the ignited specimen. A number of tests are conducted to determine the minimum concentration of oxygen that will just support combustion.

The present condensation products are useful in combination with organic polymers generally to reduce combustibility. The normally flammable organic polymers which are rendered flame retardant in accordance with the invention may be natural or synthetic but are preferably a solid synthetic polymer, more preferably a nylon or ester type polymer. Examples of the polymer are cotton, wool, silk, paper, natural rubber, and paint, and also the high molecular weight homopolymers and copolymers of amides, e.g., (nylon 66 and nylon 6). Other polymers include esters such as polyethylene terephthalate; and polymers of other unsaturated aliphatic and aromatic hydrocarbons, e.g., ethylene, propylene, butylene, sytrene, etc.; and also acrylic polymers, e.g., polyacrylonitrile, polymethyl methacrylate, alkyd resins, as well as cellulose derivatives, e.g., cellulose acetate, methyl cellulose, etc. Still other polymers include epoxy resins, furan resins, isocyanate resins such as polyurethanes, melamine resins, vinyl resins such as polyvinyl acetate and polyvinyl chloride, resorcinol resins, synthetic rubbers such as polyisoprene, polybutadiene-acrylonitrile copolymers, butadiene-styrene polymers, butyl rubber, neoprene rubber, ABS resins and mixtures thereof. Since the compositions of the invention are unusually effective flame retardants they are normally combined in flame retarding proportions with the organic polymer at relatively low concentrations, e.g., about 1-20 wt. %, preferably about 3-15% based on the weight of the total mixture, such as by milling, or impregnation, e.g., from a water or alcohol dispersion or solution, or by dissolving or dispersing in the molten polymer before extrusion such as in the form of fibers or sheets. It should be noted that it is within the scope of the invention to incorporate such ingredients as dyes, pigments, stabilizers, antioxidants, antistatic agents and the like into the novel compositions.

The following examples illustrate specific embodiments of the invention but are not restrictive of the scope of the invention:

EXAMPLE 1

In carrying out the preparation of the starting material for the polymeric phosphine oxides, a reactor is charged with one mole (63.9 grams) of n-butyllithium, in 2.1 moles of hexane as a solvent and the charge cooled to −60° C. Slow addition of one mole (235.9 grams) of paradibromobenzene is conducted over a period of 4 hours, with the mixture cooled to about −60° C, thus forming

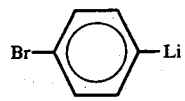

as a white slurry. Dropwise addition of 1 mole (215 grams) (C₆H₆)P(NEt₂)Cl diluted with an equal weight of tetrahydrofuran is then commenced to the about lithium compound. The symbol Et represents the ethyl group. The addition is carried out in about 4 hours of stirring. The reaction is

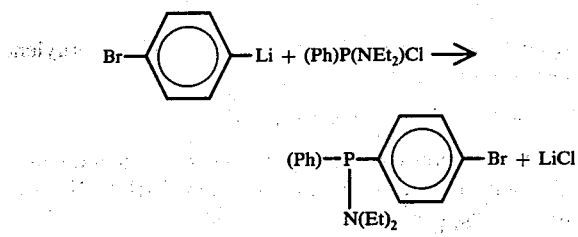

It is noted that continued addition of the phosphorus compound changes the cooled mixture from white to a beige color, with further addition giving a precipitate. The mixture is then warmed to room temperature and heated to 65° C with refluxing and stirring. During the course of the addition of the phosphorus compound some light colored solids, lithium chloride, settle out, and subsequently filtered from the liquid layer. Vacuum distillation of the liquid phase gives the product para-bromophenyl (phenyl) phosphinous diethylamide,

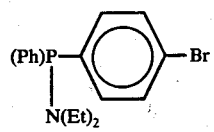

soluble in methanol, acetone, dichloromethane, trichloromethane, and dimethyl formamide. The product distills at 170° C at 0.5 mm Hg.

EXAMPLE 2

The transformation of the intermediate of Example 1 to a phosphinite product proceeds according to the following equation (where Ph is phenyl):

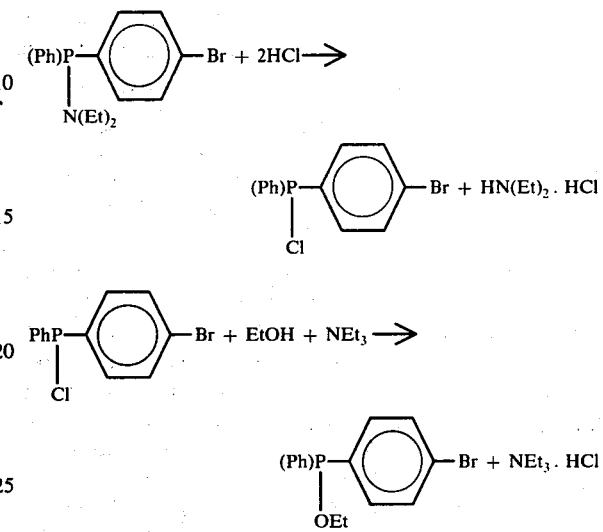

The reaction is carried out in a glass reactor by diluting the phosphorus derivative (0.406 moles, corresponding to 136.5 grams) with 1.5 liter of dry hexane. The original phosphorus compound solution is a murky brown color, although the addition of HCl (1 mol, approximately 36 grams) results in a white precipitate being formed. Absorption of the theoretical amount of HCl is monitored by watching for the appearance of HCl in the gases leaving the condenser of the reaction vessel. The reaction mixture heats up from room temperature to about 39° C during a 2.5 hour period during which the solution becomes a viscous white slurry. The slurry is further stirred for 1.5 hours while purging with a slow stream of nitrogen gas. The reaction mixture is then cooled to +5° C. Dropwise addition continues of 35 cc ethyl alcohol (0.6 moles), containing 83.6 cc of triethylamine (0.6 moles) with further dilution with dry hexane to obtain 2500 cc total volume of the solution to be added. Addition of this solution is continued over a 0.5 hour period with a further thickening of the white slurry and an exothermic reaction taking place. Settling of the reaction mixture overnight results in a white precipitate settling out. The precipitate is filtered and washed with ethyl ether, after which the filtrate is dried and distilled in vacuo and the above product identified, boiling at 130°-135° C at 0.1 mm Hg.

EXAMPLE 3

Polymerization of ethyl phenylbromophenylphosphinite is carried out utilizing a nickel bromide catalyst. A solution of 0.4 grams of nickel bromide and 25 cc of mesitylene is added in a reaction vessel together with 7.2 grams of the monomeric product of Example 2 above. The solution is maintained at refluxing conditions, with polymerization taking place at 165°-180° C. After 12 hours of heating, the reaction mixture is cooled and the green solid filtered off and purified. The polymer is dried and the molecular weight determined at 743, corresponding to 4 molecular units as shown below (more severe temperature, time and concentration condition in general, increase the molecular weight).

The polymer is soluble in ethanol (but reprecipitated by the addition of water) and in dimethylformamide; and insoluble in ethyl ether, toluene, acetone and water.

The polymer has the formula

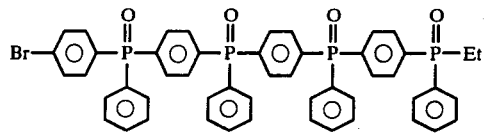

EXAMPLE 4

The polymeric phosphine oxide of Example 3 is used in an Oxygen Index Test of flame retardancy. Using a 10% addition e.g. 10 wt.% (relative to the total mixture with the modified organic polymer, polyethylene terephthalate) and with the thus modified polymer being provided as an 0.07 inch sheet, the oxygen test is 23.0. A control sample of the polyethylene terephthalate without an additive has an oxygen index level of about 19.0. A similar improvement of the flame retardancy of nylon 6,6 e.g. hexamethylene adipamide results from a 10% addition of the polymer, relative to the weight of the final modified composition. The additive does not crystallize nor oil out of the modified organic polymer.

EXAMPLE 5

The procedure of Examples 1-3 is conducted beginning with 1,4-lithiobromobenzene and $CH_3P(NMe_2)Cl$ to give the monomer

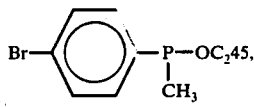

where Me is methyl.

The polymeric product is

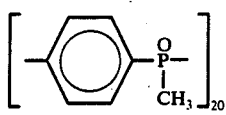

which has flame retardant properties for polyethylene terephthalate and nylon-6,6.

EXAMPLE 6

The procedure of Examples 1-3 is conducted beginning with 1,3-lithiobromobenzene and $C_3H_7P(NEt_2)Cl$ to give the monomer

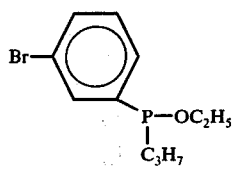

The polymeric product is

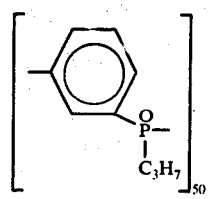

which has flame retardant properties for polyethylene terephthalate and nylon-6,6.

EXAMPLE 7

The procedure of Examples 1-3 is conducted beginning with 1,4-lithiobromonaphthalene and $CH_3P(NMe_2)Cl$ to give the monomer

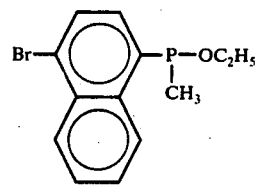

The polymeric product is

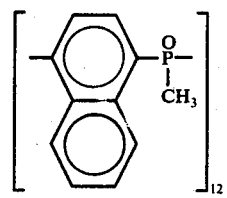

which has flame retardant properties for polyethylene terephthalate and nylon-6,6.

EXAMPLE 8

The procedure of Examples 1-3 is conducted beginning with 1,3-lithiobromobenzene and $C_{12}H_{25}P(NEt)_2Cl$ to give the monomer

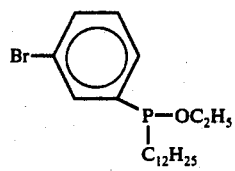

The polymeric product is

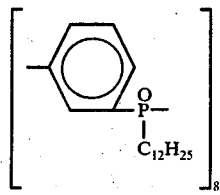

which has flame retardant properties for polyethylene terephthalate and nylon-6,6.

What is claimed is:

1. The combination of an organic polymer together with a polyphosphine oxide corresponding to the formula

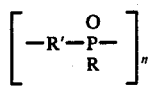

an alkyl group of 1 to 20 carbon atoms or an aryl group of 6 to 20 carbon atoms, R' is a phenylene or naphthylene group, and $n$ is from 2 to 50 units.

2. The combination of an organic polymer together with a polyphosphine oxide corresponding to the formula

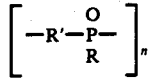

phenylene group, R is a methyl group, and $n$ is from 2 to 50 units.

3. The combination of an organic polymer together with a polyphosphine oxide corresponding to the formula

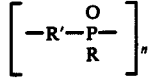

naphthylene group, R is an alkyl group of 1 to 20 carbon atoms or an aryl group of 6 to 20 carbon atoms, and $n$ is from 2 to 50 units.

4. The combination of polyethylene terephthalate together with a polyphosphine oxide corresponding to the formula

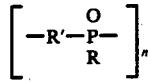

phenylene group, R is a methyl group, and $n$ is from 2 to 50 units.

5. The combination of polyethylene terephthalate together with a polyphosphine oxide corresponding to the formula

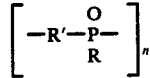

naphthylene group, R is an alkyl group of 1 to 20 carbon atoms or an aryl group of 6 to 20 carbon atoms, and $n$ is from 2 to 50 units.

6. The combination of a polyamide resin together with a polyphosphine oxide corresponding to the formula

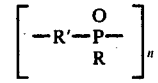

phenylene group, R is a methyl group, and $n$ is from 2 to 50 units.

7. The combination of polyamide resin together with a polyphosphine oxide corresponding to the formula

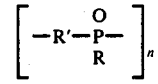

naphthylene group, R is an alkyl group of 1 to 20 carbon atoms or an aryl group of 6 to 20 carbon atoms, and $n$ is from 2 to 50 units.

8. Process for improving the flame retardancy properties of an organic polymer which comprises combining the said organic polymer with a polyphosphine oxide corresponding to the formula

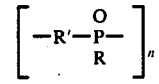

phenylene or naphthylene group, R is an alkyl group of 1 to 20 carbon atoms or an aryl group of 6 to 20 carbon atoms, and $n$ is from 2 to 50 units.

9. Process for preparing polyphosphine oxides corresponding to the formula

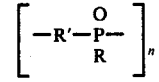

phenyl or naphthyl group, R is an alkyl group of 1 to 20 carbon atoms or an aryl group of 6 to 20 carbon atoms, and $n$ is from 2 to 50 units, which comprises dehaloalkylating in the presence of a nickel compound at a temperature of 50° C to 300° C a monomeric compound having the general formula

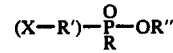

where X is chlorine or bromine, R is an alkyl group of 1 to 20 carbon atoms, or an aryl group of 6 to 20 carbon atoms, R' is phenylene or naphthylene and R" is an alkyl group of 1 to 20 carbon atoms.

* * * * *

UNITED STATES PATENT AND TRADEMARK OFFICE
CERTIFICATE OF CORRECTION

PATENT NO. : 4,072,653
DATED : February 7, 1978
INVENTOR(S) : Kurt Moedritzer

It is certified that error appears in the above-identified patent and that said Letters Patent are hereby corrected as shown below:

In Column 1, line 48 "is" should read --it--; Column 3, line 62, "on" should read --an--; Column 5, line 34, "about" should read --above--; Claim 1, line 10 after the formula
$$\begin{bmatrix} & O \\ -R'-P & \\ & R \end{bmatrix}_n$$
insert the term --wherein R is--; in each of claims 2 through 9 inclusive, after the formula
$$\begin{bmatrix} & O \\ -R'P & \\ & R \end{bmatrix}_n$$
insert the term --wherein R' is a--.

Signed and Sealed this

*Twenty-sixth* Day of *February 1980*

[SEAL]

Attest:

SIDNEY A. DIAMOND

*Attesting Officer*  *Commissioner of Patents and Trademarks*